United States Patent [19]

Pyne et al.

[11] Patent Number: 4,461,899

[45] Date of Patent: Jul. 24, 1984

[54] FLUORENECARBOXYLIC ACID DERIVATIVES

[75] Inventors: William J. Pyne; Han S. Ku, both of Painesville, Ohio; Robert E. Holm, Belle Mead, N.J.

[73] Assignee: Diamond Shamrock Chemicals Company, Dallas, Tex.

[21] Appl. No.: 381,070

[22] Filed: May 24, 1982

[51] Int. Cl.$^3$ .................. C07D 211/94; C07D 207/46; C07D 207/06

[52] U.S. Cl. .................................... 546/203; 71/94; 71/108; 71/114; 71/122; 71/126; 71/127; 548/528; 548/529; 560/8; 560/56; 562/405; 562/466; 568/808; 570/183; 585/27

[58] Field of Search ................. 546/203; 548/528, 529

[56] References Cited

U.S. PATENT DOCUMENTS

| | | | |
|---|---|---|---|
| 2,387,879 | 10/1945 | Burtner | 546/203 |
| 2,788,364 | 4/1957 | Cusic et al. | 546/203 X |
| 3,476,545 | 11/1969 | Mohr et al. | 71/76 |
| 3,506,434 | 4/1970 | Jacobi et al. | 71/89 |
| 3,598,564 | 8/1971 | Jacobi et al. | 71/76 |
| 3,646,038 | 2/1972 | Deridder | 546/203 X |
| 3,660,485 | 5/1972 | Cusic et al. | 546/203 X |
| 3,746,740 | 7/1973 | Mohr et al. | 260/469 |
| 3,830,643 | 8/1974 | Schneider et al. | 71/107 |
| 3,843,714 | 10/1974 | Schneider et al. | 260/469 |
| 3,898,239 | 8/1975 | Kyburz et al. | 546/203 |
| 3,905,972 | 9/1975 | Dostert et al. | 546/203 X |
| 4,064,347 | 12/1977 | Fleming et al. | 546/203 X |

FOREIGN PATENT DOCUMENTS 1051654 12/1966 United Kingdom .

OTHER PUBLICATIONS

March, J., *Advanced Organic Chemistry*, McGraw Hill, New York, 1968, p. 336.
Waters, J., *J. Med. Chem.*, 21,(7), 628–633,(1978).
M. Sakai, *Biochemical Toxicology of Insecticides*, Academic Press, New York, 1970, pp. 13, 16–17, 20.

*Primary Examiner*—Richard A. Schwartz
*Attorney, Agent, or Firm*—William A. Skinner; Helen P. Brush

[57] ABSTRACT

A series of ester and salt derivatives of fluorene-9-carboxylic acid and fluorene-1-carboxylic acid exhibit significant plant growth regulating properties, useful in controlling the size, shape, dormancy time, flowering time and/or fruit setting of plants, depending upon the concentrations used. They may also be used to control the growth rate, texture and color of turf grass. Presently preferred compounds include the cis-2,5-dimethylpyrrolidine salt of 1-fluorenecarboxylic acid, 9-cis-2,5-dimethyl-1-pyrrolidinyl-2-chlorofluorene-9-carboxylic acid, methyl ester, the 2,6-dimethylpiperidine salt of 1-fluorenecarboxylic acid, and the cis-2,5-dimethylpyrrolidine salt of 9-hydroxyfluorene-9-carboxylic acid.

4 Claims, No Drawings

FLUORENECARBOXYLIC ACID DERIVATIVES

BACKGROUND OF THE INVENTION

1. Field of the Invention

This invention relates to certain new compounds derived from fluorene-9-carboxylic and fluorene 1-carboxylic acids, to plant-growth regulating compositions containing these compounds and to their use for regulating plant growth.

2. Prior Art

A series of patents obtained by E. Merck AG, Darmstadt, Germany, are directed to various derivatives of fluorenecarboxylic acid useful for modifying plant growth patterns. These compounds which have become known as morphactins due to their singular mode of plant growth control, are described and/or claimed in U.S. Pat. Nos. 3,476,545; 3,598,564; 3,506,434; 3,746,740; 3,830,643; and 3,843,714. Of the many compounds described, methyl-2-chloro-9-hydroxyfluorene-9-carboxylate(chlorflurenol-methyl), in particular, has become commercially available as MAINTAIN CF-125 for use as a general plant growth retardant and weed suppressant, either by itself or in combination with other growth-affecting chemicals. However, in many instances, it has proved phytotoxic to the plants being treated.

We have now discovered and developed still different, novel derivatives of fluorenecarboxylic acid which likewise are useful as plant growth modifiers, primarily for regulating flower and fruit set in cultured plants without phytotoxic effects thereto. Particularly, those of our compounds preferred for use at this time may significantly modify the growth patterns of plants and enhance commercially important crop yields therefrom, even when employed in minute quantities.

SUMMARY OF THE INVENTION

Accordingly, the present invention is directed to various acid, ester and salt derivatives of fluorene-9-carboxylic acid and fluorene-1-carboxylic acid which exhibit significant plant growth regulating properties.

Those compounds of our invention which are acid and ester derivatives are represented by structural Formula I

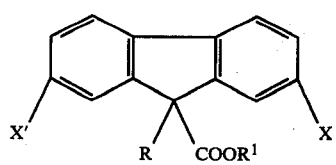

in which X and X' which may be the same or different are selected from the group consisting of H and halogen, i.e., Cl, Br or I;

R can be a 2,5-dialkylpyrrolidine group; a monoalkyl or a dialkyl piperidine group; and $R^1$ is H or $C_{1-4}$ alkyl.

Fluorenecarboxylic acid salt derivatives of this invention are represented by structural Formula II as follows:

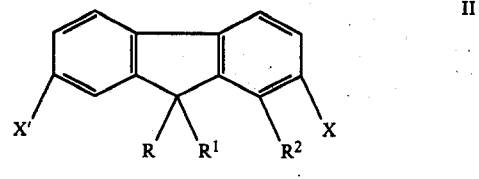

wherein X and X' have the meanings as defined above; R can be H, OH, or halogen; $R^1$ and $R^2$ each may be hydrogen or $COO^{\ominus}{}^{\oplus}R^3$, wherein $^{\oplus}R^3$ is a salt forming cation which is

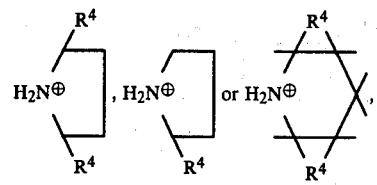

and $R^4$ is $C_{1-4}$ alkyl, with the proviso that only one of $R^1$ and $R^2$ can be $COO^{\ominus}{}^{\oplus}R^3$ at one time.

The fluorenecarboxylic acid derivatives preferred at present because of their excellent growth regulating properties conform to structural Formula III:

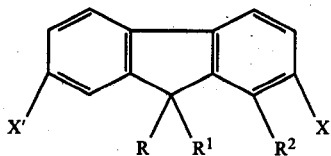

wherein X and X' may be H or halogen, i.e., Cl, Br or I;

R is H, OH or a 2,5-dialkylpyrrolidine group;

$R^1$ is H, $COO^{\ominus}{}^{\oplus}R^3$, or $COOR^4$, wherein $^{\oplus}R^3$ is a salt forming, nitrogen-containing cation selected from the group consisting of

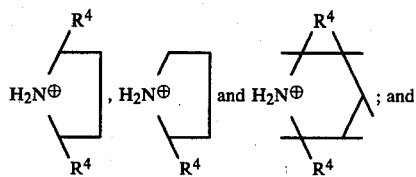

$R^4$ is H or a $C_{1-4}$ alkyl; $R^2$ is H or $COO^{\ominus}{}^{\oplus}R^3$ wherein $^{\oplus}R^3$ has the meanings as defined above, with the proviso that only one of $R^1$ and $R^2$ can be $COO^{\ominus}{}^{\oplus}R^3$ at one. time.

DESCRIPTION OF THE PREFERRED EMBODIMENTS

Specific compounds encompassed within the preferred structural formula defined above (III) include:

<u>Cis-2,5-Dimethyl-1-pyrrolidine salt of 1-fluorenecarboxylic acid</u>

-continued

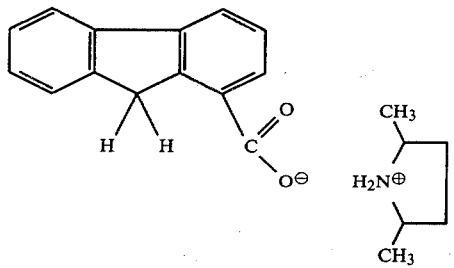

2-Methylpyrrolidine salt of 1-fluorenecarboxylic acid

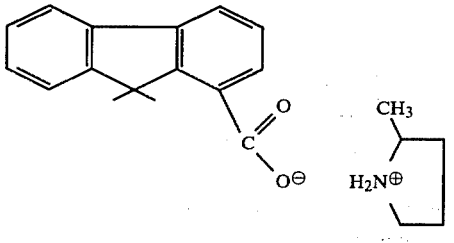

Cis-2,5-dimethylpyrrolidine salt of
2,7-dichloro-9-hydroxyfluorene-9-carboxylic acid

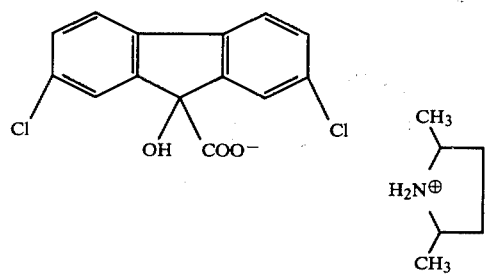

9-Cis-2,5-dimethyl-1-pyrrolidinyl-2-chlorofluorene-
9-carboxylic acid, methyl ester

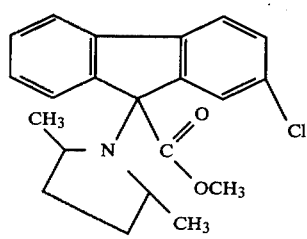

Cis-2,5-dimethyl-1-pyrrolidine salt of 9-fluorenecarboxylic acid

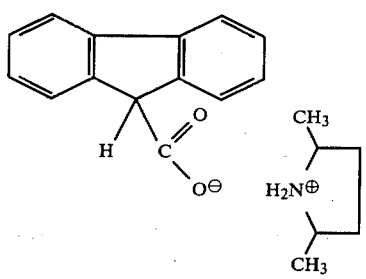

2,6-Dimethyl piperidine salt of 1-fluorenecarboxylic acid

-continued

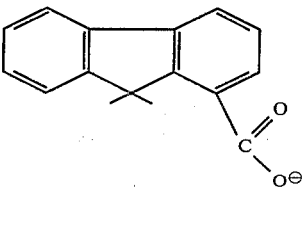 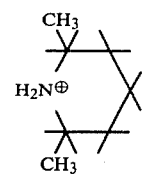

Cis-2,5-dimethylpyrrolidine salt of
9-hydroxyfluorene-9-carboxylic acid

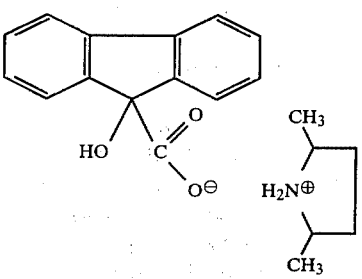 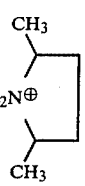

The fluorenecarboxylic acid derivatives of this invention which are lower alkyl ester compounds are obtained by standard techniques from the basic acid, i.e., by the direct esterification of the acid with excess lower alkyl alcohol. The reaction is conducted by heating the reaction mixture at reflux for two-three hours, after which the reaction mixture is cooled and the solid product separated therefrom and purified by recrystallization. These ester derivatives, normally solid at ambient temperature, typically are prepared at 85–95 percent yield.

Those fluorenecarboxylic acid derivatives of this invention which may be unsubstituted as well as monoalkyl- and dialkyl-substituted pyrrolidine or piperadine salt derivatives typically are prepared by reacting, in essentially equimolar proportions, a 9-fluorenecarboxylic acid or a 1-fluorenecarboxylic acid with the appropriate pyrrolidine or piperidine compound in a solvent medium. The solvent medium may be an aliphatic compound such as, e.g., acetone and acetonitrile, an aromatic compound such as, e.g., benzene, or a mixture of such solvents. After a slightly exothermic reaction is observed initially, the reaction solution then is briefly heated on a steam bath, e.g., for 10–30 minutes, whereupon a solid precipitates out. This is isolated, washed well and dried, preferably in air. These pyrrolidine or piperidine salt derivatives which are white to brown colored solids at ambient temperature, are typically obtained in 50–95 percent yield.

Other pyrrolidine or piperidine salt derivatives, i.e., those derived from either a 1-fluorenecarboxylic acid or a 9-fluorenecarboxylic acid which is substituted with halogen radicals, particularly in the 2,7-positions of the acid ring, are prepared by reacting such a substituted acid with the appropriate pyrrolidine or piperidine compound in an organic solvent medium for 3–6 hours at the reflux temperature of the solvent. After cooling, the solid that precipitates out is isolated, washed with water and air dried. These products likewise are obtained in 50–95 percent yield.

For application, compounds of this invention can be incorporated into all types of formulations customarily used heretofore for transporting and delivering biologically-active chemicals to plants. Thus, these compounds may be formulated in solvent-water mixtures containing surfactants. They may also be formulated as concentrated, flowable aqueous suspensions which are diluted with water prior to application. They further may be formulated as wettable powders or granules, admixed with clay, Kaolin, bentonite, ground shale, talc, chalk, and/or other adjuvants customarily employed in solid preparations. Application of any formulation can be effected by either spraying, pouring, scattering, or dusting but application of liquid materials by, e.g., spraying plant foliage, soil, etc., is presently preferred.

As true plant growth regulators, the substituted fluorenecarboxylic acid compounds of this invention may control the size, shape and/or growth rate of plants, depending upon the concentrations used. They also may control the dormancy time of plants, affecting the time of flowering and fruit maturity thereof. They may control the growth of turf grass, as well as affecting its texture and color. Also, they can improve the size, color, firmness and/or yield of fruit, including, e.g., uniform maturity thereof. Further, they can prevent preharvest drop of fruit, but they also may loosen fruit for easy harvesting in mechanical equipment. They may aid in the rooting of cuttings, as well as preventing foliage drop.

The fluorenecarboxylic acid compounds of this invention are further characterized as being non-phytotoxic to plants at the effective concentrations employed. Another important characteristic of these compounds is their extended life-time in contact with plants, soil, etc., thereby providing long-term growth regulation to the plants with no harmful residuals remaining.

For a fuller understanding of the nature of this invention, the following examples are given to illustrate the invention but are not to be taken as limiting in any sense. Unless otherwise indicated, all parts and percentages given are by weight.

EXAMPLE 1

Preparation of cis-2,5-dimethyl-1-pyrrolidine salt of 1-fluorenecarboxylic acid

1-Fluorenecarboxylic acid, 5.0 g. (0.024 mole), was dissolved in 50 mls of dry acetone. To this solution was added 2.4 g. (0.024 mole) of cis-2,5-dimethylpyrrolidine (99% of the cis-isomer). The resulting mixture was heated in a steam bath for 30 minutes after which the acetone solvent was distilled off at reduced pressure. The residual solid remaining was filtered, washed with petroleum ether and air dried. There was isolated 3.6 g. (48% of the theoretical yield) of a solid melting at 155° C. The IR spectrum confirmed that the product was a salt. That the product was the desired cis-2,5-dimethyl-1-pyrrolidine salt of fluorene-1-carboxylic acid was indicated by the following elemental analytical data; Calculated for C, 78.0%; H, 7.4%; and N, 4.50%. Found for C, 77.6%; H, 7.45%; and N, 4.49%.

EXAMPLES 2-5

Following the procedure outlined in Example 1 above, additional 1-fluorenecarboxylic acid salts were prepared by reacting with heat, the appropriate amine with the acid in acetone solvent. The residual solid product mixture remaining after distilling the solvent was, in each instance, washed in petroleum ether and air dried. Following are the results obtained:

TABLE I

| Example | Product | Yield - % | M. Pt. °C. | Elemental Analysis - % Calc. | Found |
|---|---|---|---|---|---|
| 1 | Cis-2,5-Dimethyl-1-pyrrolidine salt of 1-fluorenecarboxylic acid ($C_{14}H_{10}O_2 \cdot C_6H_{13}N_1$) | 48 | 155 | C - 78.0<br>H - 7.4<br>N - 4.50 | 77.6<br>7.45<br>4.49 |
| 2 | 2-Methyl piperidine salt of 1-fluorenecarboxylic acid ($C_{14}H_{10}O_2 \cdot C_5H_{11}N_1$) | 81 | 148–150 | C - 77.2<br>H - 7.16<br>N - 4.74 | 76.5<br>7.4<br>4.9 |
| 3 | 2,6-Dimethyl piperidine salt of fluorene-1-carboxylic acid ($C_{14}H_{10}O_2 \cdot C_7H_{15}N_1$) | 88 | 197–198 | C - 77.9<br>H - 7.79<br>N - 4.32 | 77.7<br>7.5<br>4.5 |
| 4 | Trans-2,5-dimethyl 1-pyrrolidine salt of 1-fluorenecarboxylic acid ($C_{14}H_{10}O_2 \cdot C_6H_{13}N_1$) | 78 | 170–171 | C - 78.0<br>H - 7.4<br>N - 4.50 | 77.8<br>7.8<br>4.3 |
| 5 | 4-Methyl piperidine salt of 1-fluorocarboxylic acid $C_{14}H_{10}O_2 \cdot C_6H_{13}N_1$) | 50 | 114–115 | C - 77.6<br>H - 7.5<br>N - 4.52 | 77.6<br>7.9<br>5.02 |

EXAMPLE 6

Preparation of the intermediate methyl ester of 2,9-dichlorofluorene-9-carboxylic acid 9-Hydroxyfluorene-9-carboxylic acid, 14.0 g (0.06 mol) was dissolved in excess methyl alcohol containing 5 mls of concentrated $H_2SO_4$. The resulting reaction solution was heated to reflux for 3 hours, then cooled and the excess methyl alcohol distilled off at reduced pressure. The residual solid was washed with water, air dried and then recrystallized from methyl alcohol to obtain 11 g (75% of the theoretical yield) of a yellow solid melting at 161°–162° C. An infrared spectrum of this product confirmed it to be the desired intermediate compound.

EXAMPLE 7

9-Hydroxyfluorene-9-carboxylic acid, 35 g (0.154 mol), was dissolved in 300 ml glacial acetic acid. This solution was heated to 50° C. and maintained while adding 23.8 g $Cl_2$ (0.336 mol) over a time period of 3 hours, then for an additional 1.5 hours. The crude solid was then filtered and washed well with water. It was then boiled in water briefly, filtered and dried. A pale yellow solid with a melting point of 254°–255° C. was obtained. This was confirmed by infrared spectra to be the known intermediate compound, 2,7-dichloro-9-hydroxyfluorene-9-carboxylic acid.

EXAMPLE 8

The intermediate methyl ester product of Example 6, 2.0 g (0.006 mol), was mixed with 2.94 g (0.03 mol) of cis-2,5-dimethylpyrrolidine in 45 mls of acetonitrile. This mixture was heated to reflux for 6 hours, then cooled. The solid that precipitated out was filtered, washed with water and air dried. Recovered was 2.9 g (83% of theoretical yield) of a product which, upon recrystallization from acetonitrile, melted at 130°–131° C. Elemental analysis indicated this product to be 9-cis-2,5-dimethyl-1-pyrrolidinyl-2-chlorofluorene-9-carboxylic acid, methyl ester.

EXAMPLE 9

2,7-Dichloro-9-hydroxyfluorene-9-carboxylic acid (the known Product of Example 7), 3.4 g (0.015 mol), was dissolved in 100 mls of acetone along with excess cis-2,5-dimethylpyrrolidine. This mixture was heated on a steam bath for 30 minutes, cooled and the solid that precipitated out was filtered, washed with ice cold acetone and air dried. There was isolated 3.0 g (62% of theoretical yield) of a solid which melted with decomposition at 136°–137° C. Infrared spectra showed that this product was the desired cis-2,5-dimethylpyrrolidine salt of 2,7-dichloro-9-hydroxyfluorene-9-carboxylic acid.

EXAMPLE 10

Cis-2,5-dimethylpyrrolidine, 0.61 g (0.062 mol), was mixed with 1.4 g (0.062 mol) of 9-hydroxyfluorene-9-carboxylic acid in 50 mls of dry acetone. After an initial slightly exothermic reaction, the reactant solution was heated on a steam bath for about 10 minutes. The solid that precipitated out was filtered, washed with petroleum ether and air dried. Isolated was 1.52 g, or 95% of the theoretical yield, of a white solid melting at 155° C. IR spectra and elemental analytical data indicated this product to be the desired cis-2,5-dimethylpyrrolidine salt of 9-hydroxyfluorene-9-carboxylic acid.

EXAMPLES 11–15

Other fluorenecarboxylic acid salts conforming to the structure

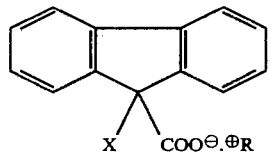

were prepared as set forth in Example 10 above, alternatively employing, as the cation-forming reactants, piperidine or 2,6-dimethylpiperidine. The following results were obtained.

TABLE II

| Example | Compound | X | +R | Yield - % | M. Pt. °C. | Elemental Analysis - % Calc. | Found |
|---|---|---|---|---|---|---|---|
| 10 | Cis-2,5-dimethyl-pyrrolidine salt of 9-hydroxyfluorene-9-carboxylic acid | OH | CH$_3$ / H$_2$N$^\oplus$ \ CH$_3$ (pyrrolidine) | 95 | 155 | C - 73.8<br>H - 7.62<br>N - 4.30 | 73.4<br>7.61<br>4.0 |
| 11 | Trans-2,5-dimethyl-pyrrolidine salt of 9-hydroxyfluorene-9-carboxylic acid | OH | CH$_3$ / H$_2$N$^\oplus$ \ CH$_3$ (pyrrolidine) | 80 | 150 | C - 73.8<br>H - 7.62<br>N - 4.30 | 73.5<br>7.1<br>4.06 |
| 12 | 2,6-dimethylpiperidine salt of 9-hydroxyfluorene-9-carboxylic acid | OH | CH$_3$ / H$_2$N$^\oplus$ \ CH$_3$ (piperidine) | 100 | 179–180 | C - 74.3<br>H - 7.42<br>N - 4.12 | 73.7<br>7.4<br>4.25 |
| 13 | 2,6-dimethylpiperidine salt of fluorene-9-carboxylic acid | H | CH$_3$ / H$_2$N$^\oplus$ \ CH$_3$ (piperidine) | 84 | 167 | C - 77.9<br>H - 7.79<br>N - 4.32 | 77.5<br>7.88<br>4.20 |
| 14 | Piperidine salt of 9-hydroxyfluorene-9-carboxylic acid | OH | H$_2$N$^\oplus$ (piperidine) | 74 | 136–137 | C - 73.3<br>H - 6.75<br>N - 4.5 | 73.3<br>6.8<br>4.55 |

TABLE II-continued

| Example | Compound | X | +R | Yield - % | M. Pt. °C. | Elemental Analysis - % Calc. | Found |
|---|---|---|---|---|---|---|---|
| 15 | Cis-2,5-dimethylpyrrolidine salt of 9-fluorenecarboxylic acid | H | CH$_3$—\\⟩—H$_2$N$^\oplus$—/—CH$_3$ | 91 | 145 | C - 78.0<br>H - 7.40<br>N - 4.80 | 77.7<br>7.45<br>4.50 |

EXAMPLE 16

The Cis-2,5-dimethylpyrrolidine salt of 1-fluorenecarboxylic acid (Product of Example 1) was tested on a six-month old Kentucky and Merion turfgrass mixture grown in 3¼" diameter waxed paper pots. Two known plant growth regulants were similarly tested. Some grass samples were not treated, only fertilized, as controls. Before treatment, the grass was cut and then fertilized with a 20-20-20 water-soluble fertilizer. Three pots were sprayed per treatment. Each chemical was dissolved in 6 ml of a mixture of 50% acetone-49.9% water-0.1% TWEEN-20 (polyoxyethylated sorbitan monolaurate surfactant manufactured by ICI United States, Inc., Wilmington, Del.) and then sprayed on the grass. The pots were placed in a plant growth room and were watered daily. The grass was cut at 21, 49 and 84 days after being treated; the blade height and total fresh weight of the clippings were measured. Tables III and IV below give the % reduction of height and weight, respectively, for the compound of this invention and the known morphactin chemicals, versus the controls. Results obtained are as follows.

TABLE III

| Dosage | Reduction in Height | | | | | | | | |
|---|---|---|---|---|---|---|---|---|---|
| | After 21 days | | | After 49 days | | | After 84 days | | |
| Kilogram/hectare | 1.12 | 2.24 | 4.48 | 1.12 | 2.24 | 4.48 | 1.12 | 2.24 | 4.48 |
| Control | 12.5 cm (5") growth | | | 13 cm (5.2") growth | | | 13.3 cm (5.3") growth | | |
| Product of Ex. 1 | 50 | 48 | 56 | 45 | 46 | 46 | 0 | 0 | 31 |
| MAINTAIN CF-125[1] | 36 | 42 | 50 | 3 | 0 | 14 | 0 | 0 | 0 |
| MOW-LESS[2] | — | — | 44 | — | — | 38 | — | — | 0 |

[1]Methyl-2-chloro-9-hydroxyfluorene-9-carboxylate
[2]Mixture of morphactin esters, manufactured by U.S. Borax

TABLE IV

| Dosage | % Reduction in Weight | | | | | | | | |
|---|---|---|---|---|---|---|---|---|---|
| | After 21 days | | | After 49 days | | | After 84 days | | |
| Kilogram/hectare | 1.12 | 2.24 | 1.12 | 1.12 | 2.24 | 4.48 | 1.12 | 2.24 | 4.48 |
| Control | (11.35 grams) | | | (10.6 grams) | | | (5.8 grams) | | |
| Product of Ex. 1 | 76 | 73 | 75 | 45 | 64 | 63 | 0 | 0 | 19 |
| MAINTAIN CF-125[1] | 31 | 38 | 52 | 0 | 0 | 4 | 0 | 0 | 0 |
| MOW-LESS[2] | — | — | 67 | — | — | 48 | — | — | 0 |

[1],[2]as previously described

As these results indicate, the compound of this invention (Product of Example 1—the cis-2,5-dimethylpyrrolidine salt of 1-fluorenecarboxylic acid), was more active in controlling grass growth than either MAINTAIN CF-125 or MOW-LESS. Further, the turf treated with this compound had a fine leaf and smooth texture; it did not have the twisted, yellowish leaves that turf treated with the known chemicals developed.

EXAMPLE 17

Two 50 cm rows of soybean plants at the early flowering stage were sprayed with 100 ppm or 500 ppm of the cis-2,5-dimethylpyrrolidine salt of 9-fluorenecarboxylic acid, using a spray volume of about 375 liters/hectare (40 gallons/acre). For comparison, other rows were sprayed with like concentrations of two known compounds as designated below. Also 2 untreated rows were maintained to serve as a control: each of the plots was weeded by hand as needed. At maturity, each plot was harvested and the yield was determined. The results obtained are as follows:

TABLE V

| Sample | Concentraton ppm | Yield (Kilograms) $\times 10^2$ | Yield Improvement % |
|---|---|---|---|
| Control | — | 17.61 | — |
| Cis-2,5-dimethylpyrrolidine salt of 1-fluorenecarboxylic (acid product of Example 1) | 100<br>500 | 19.38<br>21.98 | 9.8<br>24.1 |
| 1-fluorenecarboxylic acid | 100<br>500 | 17.16<br>17.34 | -2.7<br>-1.5 |
| 9-fluorenecarboxylic acid | 100<br>500 | 18.93<br>19.02 | 7.3<br>7.5 |

The foregoing values show that use of the compound of this invention, the cis-2,5-dimethylpyrrolidine salt of 9-fluorenecarboxylic acid, particularly at a concentration of 500 ppm, significantly enhances soybean yield over the untreated control plot and over plots treated with known morphactins, i.e., fluorenecarboxylic acids.

EXAMPLE 18

To determine fruit set effects by compounds of this invention, field grown tomato plants were foliage sprayed with the cis-2,5-dimethylpyrrolidine salt of 1-fluorenecarboxylic acid, 9-cis-2,5-dimethyl-1-pyrrolidinyl-2-chlorofluorene-9-carboxylic acid, methyl ester, and the commercial plant growth regulant, MAINTAIN CF-125 (methyl-2-chloro-9hydroxyfluorene-9-carboxylate, manufactured by U.S. Borax and Chemical Corp.). Rates of application employed were 5, 25, and 100 ppm when the tomato plants were in the late blooming to early fruit setting stage. Untreated plants were included in the test as controls. Five plants were sprayed for each chemical treatment. The number of fruit set and the degree of phytotoxicity to the plants were determined 24 days after treatment. The results obtained are as follows:

TABLE VI

| Treatment | Rate (ppm) | Fruit Set Per Plant (Initial) | (After 24 days) | Increase (%) | Increase Over Control (%) | Phytotoxicity[1] |
|---|---|---|---|---|---|---|
| Control | 0 | 9.6 | 16.6 | 73 | — | 0 |
| Product of | 5 | 7.6 | 16.2 | 108 | 35 | 0 |
| Example 1 | 25 | 11.0 | 21.0 | 91 | 18 | 0 |
|  | 100 | 10.8 | 23.8 | 120 | 47 | Light |
| Product of | 5 | 9.4 | 19.6 | 109 | 36 | 0 |
| Example 8 | 25 | 10.2 | 18.6 | 82 | 9 | 0 |
|  | 100 | 10.4 | 15.6 | 50 | (−23) | Light |
| CF-125 | 5 | 7.8 | 11.8 | 38 | (−35) | Light |
| (MAINTAIN) | 25 | 8.4 | 12.6 | 50 | (−23) | Moderate |
|  | 100 | 6.8 | 8.0 | 18 | (−55) | Heavy |

[1]Phytotoxicity: Light = some leaf epinasty; Moderate = 50% leaf epinasty; Heavy = 100% leaf curl These results show that the cis-2,5-dimethylpyrrolidine salt of 1-fluorenecarboxylic acid (Product of Example 1) increased fruit set from 18 percent to 47 percent over the control, depending upon the concentration employed. This compound caused light phytoxicity to the plants at the 100 ppm concentration. The other compound of this invention tested increased fruit set 36 percent over the control at a concentration of 5 ppm, but decreased it at the 100 ppm concentration, and also caused light phytotoxicity at this concentration. The commercial product yielded less fruit set than the control at all rates tested, while causing extensive phytotoxic effects to the treated plants.

EXAMPLE 19

This example illustrates the effects of compounds of this invention on overall yield of tomatoes. For the test, field grown tomato plants, when in the early flowering stage, were foliage sprayed with the particular compounds of the invention designated below, and with the commercial product CF-125 (Maintain), at rates of 10, 50 and 500 ppm. These rates correspond to applications of 3.69 g, 18.54 g and 185.4 g/hectare, respectively. Each treatment consisted of five plants; the experimental design was a complete randomized block with three replications. A block of untreated plants was included as the control. The fruit was harvested by hand and separated into remarkable ripe fruit and marketable green fruit. The results obtained are as follows:

TABLE VII

| Treatment | Rate (ppm) | Fruit Yield (% of Control) Red kg/hec | Green kg/hec | Total Yield (% of Control) kg/hec | Fruit Size (% of Control) Red 105.5 g | Green 104.0 g |
|---|---|---|---|---|---|---|
| Control | 0 | 16725 | 32634 | 49359 | (100%) | (100%) |
| Compounds of Invention |  |  |  |  |  |  |
| Product of | 10 | 152 | 92 | 113 | 87 | 76 |
| Example 1 | 50 | 149 | 45 | 80 | 73 | 93 |
|  | 500 | 68 | 54 | 59 | 79 | 87 |
| Product of | 10 | 134 | 33 | 67 | 80 | 104 |
| Example 10 | 50 | 119 | 61 | 81 | 100 | 101 |
|  | 500 | 226 | 80 | 129 | 108 | 65 |
| Product of | 10 | 161 | 64 | 97 | 82 | 93 |
| Example 8 | 50 | 93 | 26 | 49 | 95 | 46 |
|  | 500 | 76 | 0 | 26 | 67 | 0 |
| Product of | 10 | 119 | 45 | 70 | 161 | 137 |
| Example 3 | 50 | 122 | 69 | 128 | 165 | 101 |
|  | 500 | 127 | 86 | 59 | 127 | 83 |
| Commercial Product |  |  |  |  |  |  |
| CF-125 | 10 | 24 | 25 | 25 | 97 | 104 |
| (Maintain) | 50 | 122 | 12 | 44 | 88 | 62 |
|  | 500 | 79 | 3 | 29 | 108 | 54 |

These results show that the products of Examples 1 and 10 of this invention enhanced, at the rates applied, either the total yield of tomatoes and/or the percentage of red fruit vs. green fruit obtained, by comparison to the control. The product of Example 1, however, caused a decrease in all yields when applied at a rate of 500 ppm, while the product of Example 10 enhanced yields significantly at all three rates of application. The product of Example 8 stimulated the yield of red fruit at a rate of 10 ppm (61% over the control yield), but became inhibitory above the 50 ppm rate. In particular, the compound product of Example 3 increased the yield of red fruit at all rates of application, while also increasing the size of the fruit. On the average, the products of this invention provided greater total yields of fruit by comparison to those obtained from plants treated by the commercial product.

EXAMPLE 20

Compounds of this invention were further tested as tomato yield enhancers as follows:

"Walter" variety tomato plants, in the early flowering stage, were foliage sprayed at a rate of 68.8 liters/hectare with compounds of this invention, and with the commercial product, CF-125. Each plot consisted of 20 plants; the experimental design was a completed randomized block with three replications. A plot of untreated plants was included as a control. Marketable, mature red tomatoes were harvested weekly, beginning 5 weeks after treatment. Results are as follows:

TABLE VIII(A)

| Treatment | Rate (ppm) | Fruit Yield (kg/plot) | Total Yield Wt. % of Control |
|---|---|---|---|
| Control | — | 23.6 | = 100 (standard) |
| Product of Example 10 | 10[1] | 44.5 | 188.6 |
|  | 50 | 35.5 | 150.4 |
|  | 500 | 2.4 | 10.2 |
| Product of Example 8 | 5 | 32.8 | 139.0 |
|  | 10 | 42.6 | 180.5 |
|  | 50 | 15.4 | 65.3 |
| CF-125 (Maintain) | 5 | 25.6 | 108.0 |
|  | 10 | 15.3 | 64.8 |
|  | 50 | 2.6 | 11.0 |

[1] 10 ppm = 3.69 g/hectare; 50 ppm = 18.54 g/hectare; 500 ppm 185.4 g/hectare.

TABLE VIII(B)

| Treatment | Rate (ppm) | Harvest Time (Week) 1 | 2 | 3 | 4 | 5 | 6 | Total Fruit | % of Control |
|---|---|---|---|---|---|---|---|---|---|
| Control | 0 | 8 | 28 | 28 | 128 | 151 | 232 | 575 | = 100 |
| Product of Example 10 | 10[1] | 17 | 101 | 121 | 267 | 235 | 321 | 1062 | 185 |
|  | 50 | 18 | 122 | 73 | 168 | 193 | 266 | 840 | 146 |
|  | 500 | 8 | 29 | 11 | 2 | 1 | 9 | 60 | 10 |
| Product of Example 8 | 5 | 11 | 109 | 103 | 168 | 208 | 286 | 885 | 154 |
|  | 10 | 13 | 123 | 126 | 240 | 306 | 296 | 1104 | 192 |
|  | 50 | 34 | 150 | 81 | 25 | 9 | 100 | 399 | 69 |
| CF-125 (Maintain) | 5 | 34 | 206 | 139 | 40 | 29 | 178 | 626 | 109 |
|  | 10 | 6 | 192 | 92 | 16 | 4 | 69 | 379 | 66 |
|  | 50 | 15 | 18 | 8 | 0 | 0 | 2 | 43 | 7 |

[1] As previously described

As seen from the above results, application of 10–50 ppm of the cis-2,5-dimethylpyrrolidine salt of 9-hydroxyfluorene-9-carboxylic acid (the Product of Example 10) to the tomato plants increased the yield 50–80 percent above the yield of control plots. Application of 5–10 ppm of 9-cis-2,5-dimethyl-1-pyrrolidinyl-2-chlorofluorene-9-carboxylic acid, methyl ester (the Product of Example 8) increased tomato yields 39–80 percent above the yield of control plots. Examination of the yield patterns indicates that treatment with the aforesaid compounds at rates less than 10 and 5 ppm, respectively, would likely be beneficial to fruit yields. In all cases, use of the aforesaid compounds of this invention at the designated application rates provided yields superior to those obtained by treating the plants with the commercial product (CF-125).

What is claimed is:

1. The 2,6-dimethylpyrrolidine salt of 1-fluorenecarboxylic acid.

2. The cis-2,5-dimethyl-1-pyrrolidine salt of 1-fluorenecarboxylic acid.

3. The 2-methylpyrrolidine salt of 1-fluorenecarboxylic acid.

4. 9-cis-2,5-dimethyl-1-pyrrolidinyl-2-chlorofluorene-9-carboxylic acid, methyl ester.

* * * * *

UNITED STATES PATENT AND TRADEMARK OFFICE
CERTIFICATE OF CORRECTION

PATENT NO. : 4,461,899
DATED : July 24, 1984
INVENTOR(S) : William J. Pyne et al It is certified that error appears in the above-identified patent and that said Letters Patent are hereby corrected as shown below:

Column 9, TABLE III, insert "%" before "Reduction in Height".

Column 10, TABLE V, correct the spelling of "Concentration".

Column 14, Claim 1, line 1, change -- 2,6-dimethylpyrrolidine -- to "2,6-dimethylpiperidine".

Signed and Sealed this

Twenty-sixth Day of March 1985

[SEAL]

Attest:

DONALD J. QUIGG

Attesting Officer     Acting Commissioner of Patents and Trademarks